(12) United States Patent
Lee (10) Patent No.: US 11,389,643 B2
(45) Date of Patent: *Jul. 19, 2022

(54) ELECTRIC DEVICE FOR MEASURING EEG SIGNAL OR ELECTRIC STIMULATION

(71) Applicant: YBRAIN INC., Seongnam (KR)

(72) Inventor: Kiwon Lee, Seongnam (KR)

(73) Assignee: YBRAIN INC., Seongnam (KR)

( * ) Notice: Subject to any disclaimer, the term of this patent is extended or adjusted under 35 U.S.C. 154(b) by 599 days.

This patent is subject to a terminal disclaimer.

(21) Appl. No.: 16/271,262

(22) Filed: Feb. 8, 2019

(65) Prior Publication Data
US 2019/0167974 A1    Jun. 6, 2019

Related U.S. Application Data

(63) Continuation of application No. 14/934,448, filed on Nov. 6, 2015, now Pat. No. 10,245,425.

(30) Foreign Application Priority Data

Nov. 27, 2014  (KR) .................. 10-2014-0167502

(51) Int. Cl.
*A61B 5/291*        (2021.01)
*A61N 1/04*         (2006.01)
(Continued)

(52) U.S. Cl.
CPC ........... *A61N 1/0476* (2013.01); *A61B 5/291* (2021.01); *A61N 1/0484* (2013.01);
(Continued)

(58) Field of Classification Search
None
See application file for complete search history.

(56) References Cited

U.S. PATENT DOCUMENTS 4,977,896 A * 12/1990 Robinson ............... A61B 5/242
600/409
5,981,268 A   11/1999 Kovacs et al.
(Continued)

FOREIGN PATENT DOCUMENTS

JP      2004-512127 A    4/2004
JP      2007-515200 A    6/2007
KR   10-2011-0064071 A    6/2011

OTHER PUBLICATIONS

Korean Office Action for application No. 10-2014-0167502 dated Feb. 13, 2015.
(Continued)

*Primary Examiner* — Michael R Bloch
(74) *Attorney, Agent, or Firm* — Studebaker & Brackett PC (57) ABSTRACT

Disclosed is an electronic device for measuring EEG signal, including: a plurality of electrode units configured to be attached to each different position of the head of the subject and configured to detect the EEG signal from the subject's head, and wherein each of the plurality of electrode units includes a plurality of microelectrodes forming an electric array, a switching unit connected to the plurality of electrode units, and configured to switch the each of the plurality of electrode units to be selectively connected and each of the plurality of microelectrodes to be selectively connected, and a controller connected to the switching unit, and configured to control the switching unit to be selectively connected to the each of the plurality of the electrode units to receive the EEG signal from the subject's head through connected electrode unit among the plurality of electrode units.

7 Claims, 5 Drawing Sheets

(51) Int. Cl.
*A61N 1/36* (2006.01)
*A61B 5/00* (2006.01)
*A61B 5/316* (2021.01)

(52) U.S. Cl.
CPC .......... *A61N 1/36025* (2013.01); *A61B 5/316* (2021.01); *A61B 5/6803* (2013.01); *A61B 2562/046* (2013.01)

(56) References Cited

U.S. PATENT DOCUMENTS

| | | | |
|---|---|---|---|
| 6,230,049 B1 | 5/2001 | Fischell et al. | |
| 7,208,077 B1 | 4/2007 | Albers et al. | |
| 8,280,502 B2 | 10/2012 | Hargrove et al. | |
| 8,588,884 B2* | 11/2013 | Hegde | A61B 5/25 600/372 |
| 2004/0013291 A1 | 1/2004 | Hillman | |
| 2006/0122523 A1 | 6/2006 | Bonmassar et al. | |
| 2006/0173510 A1* | 8/2006 | Besio | A61B 5/375 607/45 |
| 2007/0123765 A1 | 5/2007 | Hetke et al. | |
| 2008/0270188 A1 | 10/2008 | Garg et al. | |
| 2009/0030476 A1* | 1/2009 | Hargrove | A61N 1/36031 607/40 |
| 2011/0224752 A1* | 9/2011 | Rolston | A61N 1/0529 607/45 |
| 2011/0288610 A1 | 11/2011 | Brocke | |
| 2011/0295350 A1 | 12/2011 | Mercanzini et al. | |
| 2011/0313270 A1 | 12/2011 | Pereira Neves et al. | |
| 2012/0277834 A1 | 11/2012 | Mercanzini et al. | |
| 2013/0085361 A1 | 4/2013 | Mercanzini et al. | |
| 2013/0304407 A1* | 11/2013 | George | A61B 5/7246 702/72 |
| 2014/0350431 A1 | 11/2014 | Hagedorn | |
| 2015/0289778 A1 | 10/2015 | Ohl et al. | |
| 2015/0297108 A1 | 10/2015 | Chase et al. | |

OTHER PUBLICATIONS

Korean Notice of Allowance for 10-2014-0167502 dated May 19, 2015.

* cited by examiner

ELECTRIC DEVICE FOR MEASURING EEG SIGNAL OR ELECTRIC STIMULATION

CROSS-REFERENCE TO RELATED APPLICATION

The present application is a continuation of U.S. patent application Ser. No. 14/934,448, filed on Nov. 6, 2015, which claims priority from Korean Patent No. 10-1539654 (Korean Patent Application No. 10-2014-0167502), filed on Nov. 27, 2014 and registered on Jul. 21, 2015 in the Korean Intellectual Property Office. The disclosures of the above parent application and Korean Patent are incorporated herein by reference in its entirety.

TECHNICAL FIELD

The present invention relates to an electric device for measuring EEG signal or electric stimulation, and more particularly, an electric device for measuring EEG signal from a subject's head or for applying electric stimulation to the head by using a plurality of microelectrodes forming an electrode array.

RELATED ART

The statements in this section merely provide information related to the present disclosure and do not necessarily constitute prior art.

It is known that a technology for electric stimulation by using transcranial Direct Current Stimulation (tDCS) is effective in cognition improvement and treatment for depression and Attention Deficit Hyperactivity Disorder (ADHD).

According to a technology for measuring Electroencephalogram (EEG), the brain activity can be predicted by measuring the potential change of the scalp in relation to brain activities.

Therefore, utilizing technology for electric stimulation of brain in everyday life would help improving the brain function, and enable the treatment for chronic mental illnesses by activating or controlling the connection between the nerves. Moreover, utilizing such technology in everyday life would also enable detecting abnormality of brain or brain seizure, infection or metabolic diseases.

SUMMARY

The conventional EEG measuring device or tDCS device include a plurality of electrodes; using a single electrode as a measuring or stimulation module, it measures EEG signals from different positions of the head, or applies electric stimulation thereto.

However, since a measuring or stimulating position is limited only to the area on the head where the electrode is attached when a user wears the device on the head, it is difficult for the user to accurately adjust the measuring or stimulating position unless wearing the device again on the other position. Therefore, the conventional device for measuring EEG signal or tDCS device cannot readily optimize the position for measuring EEG signals or electric stimulation.

An object of the present invention devised to solve the above-mentioned conventional problem is to provide an electric device enabling detailed adjustment of a measuring or stimulating position by using a plurality of microelectrodes forming an electric array when measuring an EEG signal or applying electric stimulation to a subject's head.

It is a further object of the present invention to provide an electric device, wherein an EEG measuring device and an electric stimulation device are combined, for measuring an EEG signal from a subject's head or applying electric stimulation thereto, It is yet another object of the present invention to provide an electric device for estimating an EEG signal for the area of the head to which a plurality of the electrodes is not directly attached.

The objects of the present invention are not limited to the above-mentioned, and the other objects not mentioned herein will be readily apparent to those skilled in the art from the description to follow.

In accordance with an embodiment of the present invention, an electric device for measuring EEG signal from a subject's head comprises: a plurality of electrode units configured to be attached to each different position of the head of the subject and configured to detect the EEG signal from the subject's head, and wherein each of the plurality of electrode units includes a plurality of microelectrodes forming an electric array; a switching unit connected to the plurality of electrode units, and configured to switch the each of the plurality of electrode units to be selectively connected and each of the plurality of microelectrodes to be selectively connected; and a controller connected to the switching unit, and configured to control the switching unit to be selectively connected to the each of the plurality of the electrode units to receive the EEG signal from the subject's head through connected electrode unit among the plurality of electrode units, wherein the controller is configured to receive a first plurality of EEG signals detected from first plurality of microelectrodes included in first electrode unit among the plurality of electrode units, receive the first plurality of EEG signals detected from first area of the subject's head, through the switching unit, calculate a changing tendency by analyzing the first plurality of EEG signals detected from first area of the subject's head, and predict a second plurality of EEG signals in a second area of the subject's head separated from the first electrode unit, based on calculated changing tendency.

BRIEF DESCRIPTION OF DRAWINGS

The above and/or other aspects will become apparent and more readily appreciated from the following description of exemplary embodiments, taken in conjunction with the accompanying drawings of which.

DETAILED DESCRIPTION

Reference will now be made in detail to exemplary embodiments, examples of which are illustrated in the accompanying drawings. However, the present inventive concept may be embodied in many different forms and should not be construed as being limited to the exemplary embodiments set forth herein. Rather, these exemplary embodiments are provided so that the present disclosure will be thorough and complete, and will fully convey the scope of the present inventive concept to those skilled in the art, and the spirit and scope of the present inventive concept should be defined by the appended claims.

Without separate definitions, all terms (including technical and scientific terms) used in the present description may be used for the meanings commonly understandable to those having ordinary skill in the art. In addition, the terms generally used and having definitions in dictionary, unless otherwise defined obviously in particular, should not be ideally or exaggeratedly interpreted.

The terms used in the present description are to explain the exemplary embodiments, not to limit the present invention thereto. In the present description, a singular form of word also includes a plural form thereof unless otherwise noted. The term "comprises" and/or "comprising" is not excluding the meaning that one or more elements other than the said element may exist or be added.

Hereinafter, exemplary embodiments of the present inventive concept will be described in detail with reference to the accompanying drawings. In the drawings, like reference numerals refer to like elements.

The term 'module' used hereinafter may indicate a hardware configuration while a part thereof may be a functional module embodied in software.

The term 'electric stimulation' used hereinafter may indicate a transcranial Current Stimulation (tCS), but the meaning is not limited thereto.

In reference with the drawings, the electric device according to the exemplary embodiments of the present invention will be described in detail.

Figure 1:
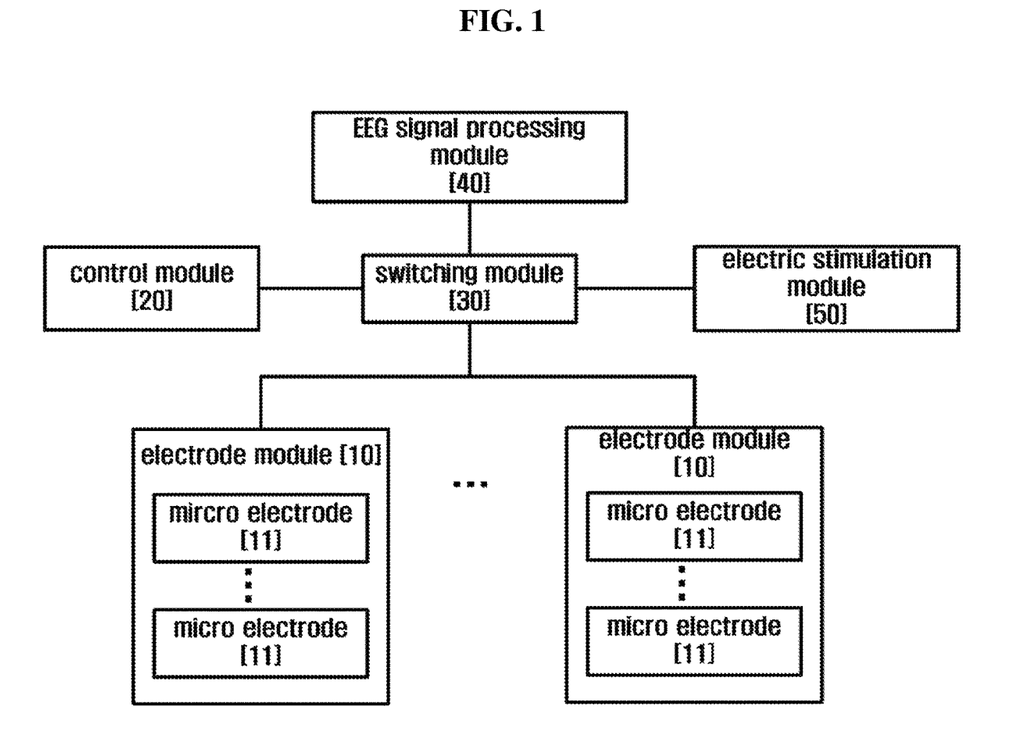
FIG. 1 is a diagram illustrating an outline configuration of the electric device according to the first exemplary embodiment of the present invention.
Figure 2:
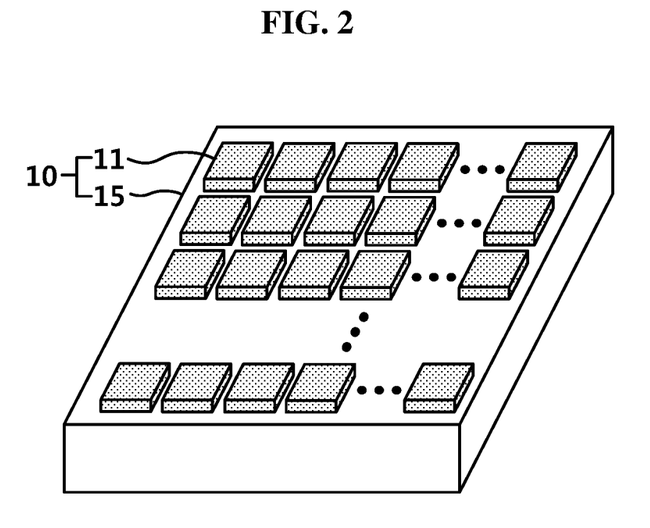
FIGS. 2 and 3 are perspective diagrams of an electrode module 10 included in FIG. 1.
Figure 3:
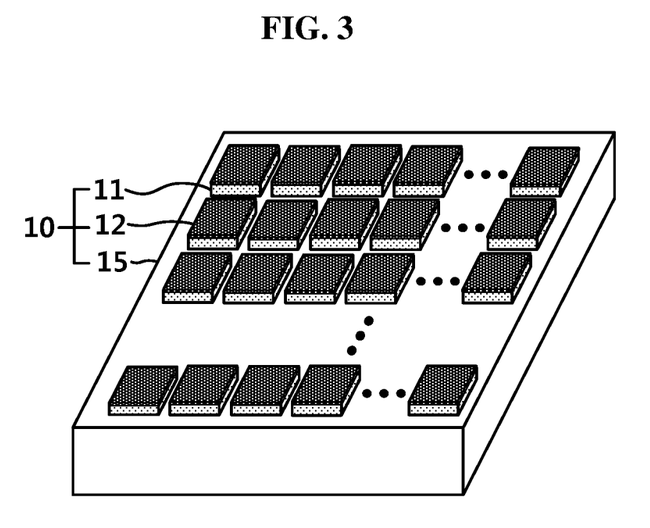

In reference with FIG. 1 to FIG. 3, the electric device according to a first exemplary embodiment of the present invention will be described in the following. FIG. 1 is a diagram illustrating an outline configuration of the electric device according to the first exemplary embodiment of the present invention. FIG. 2 and FIG. 3 are perspective diagrams of an electrode module 10 included in FIG. 1.

The electric device, according to the first exemplary embodiment of the present invention, can measure an EEG signal from a subject's head or apply electric stimulation thereto. In particular, an electrode module 10 of the electric device according to the present exemplary embodiment measures an EEG signal from a subject's head or applies electric stimulation thereto by using a plurality of microelectrodes 11 forming an electrode array, thereby accurately controlling a measuring or stimulating position. Therefore, it is possible for the electric device, according to the first exemplary embodiment of the present invention, to optimize a measuring or stimulating position.

In reference with FIG. 1, the electric device, according to the present exemplary embodiment, may include an electrode module 10, a control module 20, a switching module 30, an EEG signal processing module 40, and an electric stimulation module 50. However, the components shown by FIG. 1 are not the essential; more components, or less, than the aforementioned may be included to form the electric device.

An electrode module 10, attached to a subject's head, detects an EEG signal from the head or applies current thereto, which means the electrode module 10 not only detects an EEG signal from the head, and applies current thereto, respectively, but also the electrode module 10 may detect an EEG signal while applying current at the same time.

More than one electrode module 10 may be included in the electric device; according to the present exemplary embodiment, the electric device, including a plurality of electrode modules 10, can detect an EEG signal from a plurality of positions on a subject's head or apply electric stimulation thereto. However, the configuration is not limited to the above-mentioned; the electric device may include a single electrode module 10. A subject, to whom the electric device is used, can have an EEG signal measured or receive electric stimulation by using the electric device.

In particular, when a subject wears the electric device or has it attached to the head, the electrode module 10 can be attached to the subject's head, and a plurality of the electrode modules 10, attached to each different position on the subject's head, detect EEG signals from the subject's head (brain) or apply current thereto.

According to a control module 20 which will appear hereafter, all the electrode modules 10 may detect EEG signals from a subject's head, or apply current to the head, simultaneously. However, the method is not limited to the above-mentioned; a part of a plurality of the electrode modules 10 may operate and the others may not. Also, a part of a plurality of the electrode modules 10 may detect EEG signals from a subject's head while the others apply current to the head at the same time. In addition, according to several exemplary embodiments, an electrode module 10 may detect an EEG signal from a subject's head while applying current to the head at the same time.

Meanwhile, in reference with FIG. 1 and FIG. 2, each electrode module 10 may include a plurality of microelectrodes 11 forming an electrode array.

A plurality of the microelectrodes 11 included in a single electrode module 10, located adjacent to each other, form an electrode array or a group. For example, according to several exemplary embodiments, a plurality of the microelectrodes 11 forming an electrode array can be arranged on the same circuit board 15. Nevertheless, each of the microelectrodes 11, electrically separate from each other, can be individually controlled by the control module 20 which will appear hereafter.

Since the electrode module 10 includes a plurality of microelectrodes 11, the area which had once been controlled by a single electrode of the conventional device, can be divided into a plurality of small areas which can be controlled by each microelectrode 11. Accordingly, smaller area can be a standard module operating an EEG signal measurement or electric stimulation, enabling the electric device to accurately control a measuring or stimulating position, according to the first exemplary embodiment of the present invention.

A microelectrode 11 can detect an EEG signal from a subject's head, or apply current to the head, which means not only the microelectrode 11 can measure an EEG signal from the subject's head, and apply current to the head, independently, but also the microelectrode 11 can detect an EEG signal while applying current at the same time.

Each of the microelectrodes 11 operates individually because a plurality of the microelectrodes 11 included in a single electrode module 10 are neither connected to each other nor operating in the same way.

According to a control module 20 which will appear hereafter, all the microelectrodes 11, included in a single electrode module 10, may detect EEG signals from a subject's head or apply current to the head simultaneously.

However, the method is not limited to the above-mentioned; only a part of the microelectrodes 11 may operate while the others may not. Also, a part of a plurality of the microelectrodes 11 may detect an EEG signal from a subject's head when the others apply current to the head at the same time. According to several exemplary embodiments, one or more than one microelectrode 11 may detect an EEG signal from a subject's head while applying current to the head at the same time.

Meanwhile, in reference with FIG. 3, a patch 12 may be formed on a plurality of the microelectrodes 11 according to several exemplary embodiments. That is, the patch 12 formed on the neighboring microelectrodes 11, separated from each other, may prevent the neighboring microelectrodes 11 from affecting to each other during the EEG signal measurement or the electric stimulation.

The patch 12 may be directly attached to a subject's scalp, and include a hydrogel containing chlorine ion. The skin and the patch 12 attached thereto become having a common ion as the skin also includes chlorine ion. Accordingly, by lowering the over-potential, formed between the microelectrode 11 and the skin, unnecessary amount of stimulation to the skin can be avoided. According to the present exemplary embodiment, the electric device can prevent the scalp from having skin-burn when detecting the EEG signal from a subject's head or applying electric stimulation thereto.

A control module 20 can control an overall electric device, including a plurality of electrode modules 10. For example, the control module 20 can control each electrode module 10 included in a plurality of the electrode modules 10 so as to detect an EEG signal from a subject's head and applying current to the head, which means each electrode module 10 can be controlled not only for detecting an EEG signal from a subject's head, and for applying current to the head, respectively, but also for detecting an EEG signal and applying current to the head at the same time.

Since each electrode module 10 includes a plurality of microelectrodes 11 forming an electrode array, the control module 20 controls each electrode module 10 so as to detect an EEG signal from a subject's head or applying current to the head by means of controlling each of a plurality of the microelectrodes 11, included in each electrode module 10, so as to detect an EEG signal from a subject's head or apply current thereto. That is, the control module 20 controls each of a plurality of the microelectrodes 11 not only for detecting an EEG signal from a subject's head and for applying current to the head, respectively, but also for detecting an EEG signal and applying current to the head at the same time.

In particular, the control module 20 may control a plurality of electrode modules 10 and a plurality of the microelectrodes 11 included in each of a plurality of the electrode modules 10 by controlling the relationship between a plurality of the electrode modules 10 and a plurality of the microelectrodes 11.

In particular, in reference with FIG. 1 showing the connection structure of the electric device according to the present invention, a plurality of the electrode modules 10 are connected with a switching module 30, and the switching module 30 is connected with an EEG signal processing module 40 processing the EEG signal detected by a plurality of the electrode modules 10, and with an electric stimulation module 50 providing a plurality of the electrode modules 10 with current for electric stimulation. Also, the switching module 30, connected with the control module 20, can be controlled by the control module 20. Although not shown by the drawing, the EEG signal processing module 40 and the electric stimulation module 50, connected with the control module 20, can also be controlled by the control module 20 as necessary.

Accordingly, by controlling the switching module 30, the control module 20 determines whether a plurality of the electrode modules 10, and particularly a plurality of the microelectrodes 11 included in each electrode module 10, should be connected with the EEG signal processing module 40 or with the electric stimulation module 50. Meanwhile, according to circumstances, the control module 20 can control a specific electrode module 10 or a specific microelectrode 11 so as to be connected with neither the EEG signal processing module 40 nor the electric stimulation module 50, thereby making them not to implement anything. In addition, the control module 20 can control a specific electrode module 10 or a specific microelectrode 11 so as to be connected with the EEG signal processing module 40 and the electric stimulation module 50 simultaneously, thereby making them implement the EEG signal measurement and the electric stimulation at the same time.

Therefore, for the control module 20, controlling each electrode module 10 or each microelectrode 11 for detecting an EEG signal from a subject's head or applying current to the head may be the same with determining whether each electrode module 10 or each microelectrode 11 to be connected with the EEG signal processing module 40 or the electric stimulation module 50. At this, determining whether each electrode module 10 or each microelectrode 11 to be connected with the EEG signal processing module 40 or the electric stimulation module 50 may be selecting one from the options such as connecting each electrode module 10 or each microelectrode 11 with the EEG signal processing module 40; connecting it with the electric stimulation module 50; connecting it with the EEG signal processing module 40 and the electric stimulation module 50 simultaneously; and connecting it with neither of them.

A switching module 30, as previously described, can control the electrode module 10, and particularly the relationship of the microelectrode 11. In order for this, the switching module 30, receiving a control signal from the control module 20, can control the relationship between the components. According to several exemplary embodiments, the switching module 30 may include a multiplexer, but the configuration of the switching module 30 is not limited thereto.

An EEG signal processing module 40 can process the EEG signal detected by a plurality of the electrode modules 10. For example, the EEG signal processing module 40 receives the EEG signal detected by a plurality of the electrode modules 10, and analyzes the received EEG signal. In order for this, the EEG signal processing module 40 may include a database (not shown), and save the received EEG signal and the result of the analysis in the database. But the process is not limited to the above-mentioned.

Meanwhile, the control module 20 controls the switching module 30 so as to connect a specific electrode module 10, and particularly a specific microelectrode 11 with the EEG signal processing module 40, thereby operating the electrode module 10, and more particularly the microelectrode 11 for detecting an EEG signal from a subject's head.

Besides, according to several exemplary embodiments, the EEG signal processing module 40 may include a blocking filter (not shown). The blocking filter is to prevent the distortion in the EEG signal measurement due to electric stimulation when measuring an EEG signal and the electric stimulation are carried out by the same microelectrode 11 or those adjacent to each other.

The blocking filter, for example, can be formed in software in order to receive the information regarding an electric stimulation signal or a protocol for electric stimulation from the electric stimulation module 50 and to remove the electric stimulation signal or the protocol for electric stimulation received from the measured EEG signal. However, the configuration is not limited to the above-mentioned; in case of the electric stimulation signal or the protocol for electric stimulation being a signal of direct current and the EEG signal being a signal of alternating current, the blocking filter can be formed in hardware in order to block the signal of direct current.

An electric stimulation module 50 can provide a plurality of the electrode modules 10 with current for electric stimulation. For example, the electric stimulation module 50 can generate a protocol for electric stimulation, and provide each of the microelectrodes 11 with current for electric stimulation, according to the generated protocol.

Meanwhile, the control module 20 controls the switching module 30 so as to connect a specific electrode module 10, more particularly a specific microelectrode 11, with the electric stimulation module 50, thereby operating the electrode module 10, more particularly the microelectrode 11, for applying current to a subject's head.

The operation of the electric device, according to the first exemplary embodiment of the present invention, will be explained in the following. However, the operation of the electric device is not limited to the content which follows.

[Optimization of the Position for Measuring EEG Signal]

When a subject wears the electric device on the head, it is possible to determine where in the head the electrode module 10 is to attach. When the subject wears the electric device for the first time, he/she may wear it in a way that the electrode being attached on the desired position for measuring an EEG signal. However, it may be needed to adjust a measuring position due to different head shapes depending on the person.

Since a single electrode module 10 includes a plurality of microelectrodes 11 forming an electrode array, the electric device, according to the first exemplary embodiment of the present invention, can accurately adjust the position for measuring an EEG signal, thereby optimizing the position for measuring an EEG signal.

That is, the control module 20, based on the EEG signal detected by a plurality of the microelectrodes 11 included in at least one electrode module 10 selected from a plurality of electrode modules 10, can determine at least one microelectrode 11, selected from a plurality of the microelectrodes 11 included in the electrode module 10, to control for detecting an EEG signal from a subject's head.

Above all, the control module 20 can detect an EEG signal from each of the microelectrodes 11. For example, each microelectrode 11 may detect an EEG signal in order, but the method is not limited thereto.

Subsequently, the control module 20, based on the detected EEG signal, can determine which microelectrode 11 to use for detecting an EEG signal. For example, by using the result of comparing the EEG signal detected by each microelectrode 11 with a standard EEG signal, the control module 20 can determine at least one microelectrode 11 to use for detecting the EEG signal from a subject's head. At this, a standard EEG signal, as an EEG signal to be measured or to be received from the desired position for measuring, can be a standard for comparison. Therefore, as a result of comparing the EEG signal detected by each microelectrode 11 with the standard EEG signal, the EEG signal having the highest matching rate with the standard EEG signal or having the matching rate above a certain figure can be determined, and the microelectrode 11 which detected such EEG signal can be determined as a microelectrode 11 to be used for detecting an EEG signal.

However, the process is not limited to the above-mentioned; by using the result of comparing the signal strength between the EEG signals detected by each microelectrode 11, at least one microelectrode 11 can be determined to be used for detecting an EEG signal from a subject's head. In other words, the EEG signal having the highest signal strength or having the signal strength above a certain figure can be determined, and the microelectrode 11 which detected such EEG signal can be determined as a microelectrode to be used for detecting an EEG signal.

Therefore, the electric device, according to the first exemplary embodiment of the present invention, detects an EEG signal by using the determined microelectrode 11, thereby measuring the desired EEG signal at the optimized position.

[Optimization of the Position for Applying Electric Stimulation]

As previously described, the electric device according to the first exemplary embodiment can find the exact position for measuring an EEG signal. In the similar way, the position for applying electric stimulation can be optimized as well.

In particular, the control module 20, based on the EEG signal detected by a plurality of the microelectrodes 11 included in at least one electrode module 10 selected from a plurality of electrode modules 10, can determine at least one microelectrode 11, selected from a plurality of the microelectrodes 11 included in the electrode module 10, to control in order to apply current to a subject's head.

In particular, the control module 20 can, above all, detect an EEG signal by each microelectrode 11. For example, the control module may detect the EEG signal by each of the microelectrodes 11 in order; however, the method is not limited thereto.

Subsequently, the control module 20, based on the detected EEG signal, can determine the microelectrode 11 to be used for detecting an EEG signal. For example, by using the result of comparing the EEG signal detected by each microelectrode 11 with a standard EEG signal, at least one microelectrode 11 can be determined to be used for detecting the EEG signal from a subject's head. At this, a standard EEG signal, as an EEG signal which can be received from the area determined as a stimulating position, can be a standard for comparison. Therefore, as a result of comparing the EEG signal detected by each microelectrode 11 with the standard EEG signal, the EEG signal having the highest matching rate with the standard EEG signal or having the matching rate above a certain figure can be determined, and the microelectrode 11 which detected such EEG signal can be determined as a microelectrode 11 to be used for electric stimulation.

Meanwhile, according to several exemplary embodiments, when the electric stimulation is set to apply to the area of the size as much as pre-set, the control module 20 can calculate the number of the microelectrode 11 necessary for electric stimulation with consideration of the size of a single microelectrode 11, and accordingly determine at least one micro stimulation to be used for electric stimulation.

Therefore, the electric device according to the first exemplary embodiment of the present invention can apply electric stimulation by using the selected microelectrode 11, thereby applying the electric stimulation in the optimized position.

[Estimation of the EEG Signal]

The electrode module 10 according to the first exemplary embodiment of the present invention may include a plurality of microelectrodes 11 forming an electrode array. Therefore, by using a plurality of the microelectrodes 11 it can measure an EEG signal from a subject's head. On the basis of a plurality of the measured EEG signals, the information regarding the changing tendency of the EEG signals in the area within a certain range of the head can be obtained.

Therefore, the control module 20, based on the EEG signal detected by a plurality of the microelectrodes 11 included in at least one electrode module 10 selected from a plurality of electrode modules 10, can predict the EEG signal in the area separate from the electrode module 10.

In particular, the control module 20 can obtain the information on the EEG signal for each position within the range of the area from a plurality of the microelectrodes 11 included in a single electrode module 10, and it can analyze such information, thereby calculating the changing tendency of the detected EEG signals for the area to which the electrode module 10 is attached.

On the basis of the calculated changing tendency, the EEG signal for the area separated from the electrode module 10 can be predicted. That is, by discovering the information regarding how far and in which direction the specific area of the head for predicting the EEG signal is separated from the area of the head attached to the electrode module 10 and by substituting such information regarding the direction and distance to the changing tendency of the EEG signal, it is possible to estimate the EEG signal in the area separated from the electrode module 10.

Therefore, the electric device, according to the first exemplary embodiment of the present invention, enables estimating the EEG signal measured from the area which despite is not directly attached to the electrode module 10.

Figure 4:
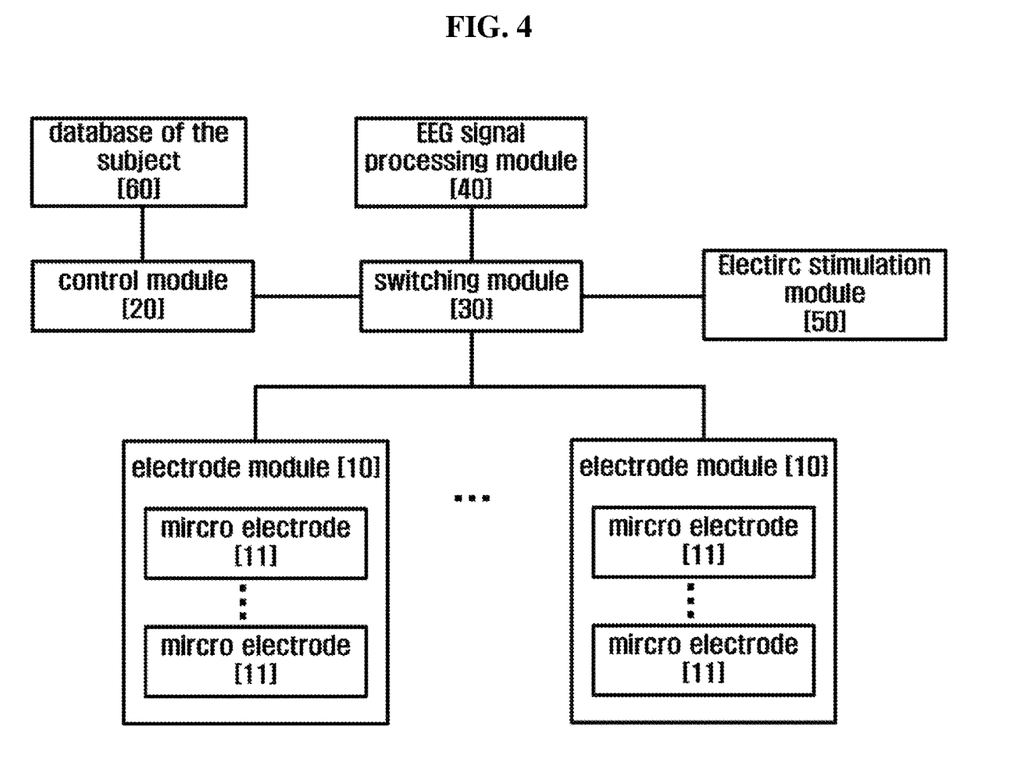
FIG. 4 is a diagram illustrating an outline configuration of the electric device according to the second exemplary embodiment of the present invention.

In reference with FIG. 4, the electric device according to a second exemplary embodiment of the present invention will be explained in the following. FIG. 4 is a diagram illustrating an outline configuration of the electric device according to the second exemplary embodiment of the present invention. The description which follows will be mainly focused only on the difference from the electric device according to the first exemplary embodiment of the present invention.

In reference with FIG. 4, the electric device according to the second exemplary embodiment of the present invention may further include a database 60 already storing a subject's EEG data. The previously analyzed EEG data on the subject may be saved in the database 60.

The control module 20, on the basis of the EEG signal detected by a plurality of the microelectrodes 11 included in at least one electrode module 10 selected from a plurality of the electrode modules 10, can discover where in the head of the subject the electrode module 10 is attached by comparing the detected EEG signal with the EEG data saved in advance in the database 60.

As previously described, the EEG data on the subject are saved in the database 60, and the information regarding which data can be obtained and where in the head of the subject the data can be obtained can be saved therein in advance. Therefore, the EEG signal can be measured by using the microelectrode 11 included in the electrode module 10, and the control module 20 can check on the database 60 to see whether the EEG data corresponding to the measured EEG signal is available. In the case where the corresponding EEG data were found, it is possible to check which area of the head the data are corresponding to. Accordingly, the position for wearing the electric device can be recognized by checking which area of the head the electrode module 10 of the electric device is attached to.

In several exemplary embodiments, when the adjustment of the position for wearing the device is needed, the electric device may provide a direction on how to adjust the position in voice or on display. And, as necessary, the electric device may send the information regarding the wearing position and adjustment guide to the subject's own device.

Figure 5:
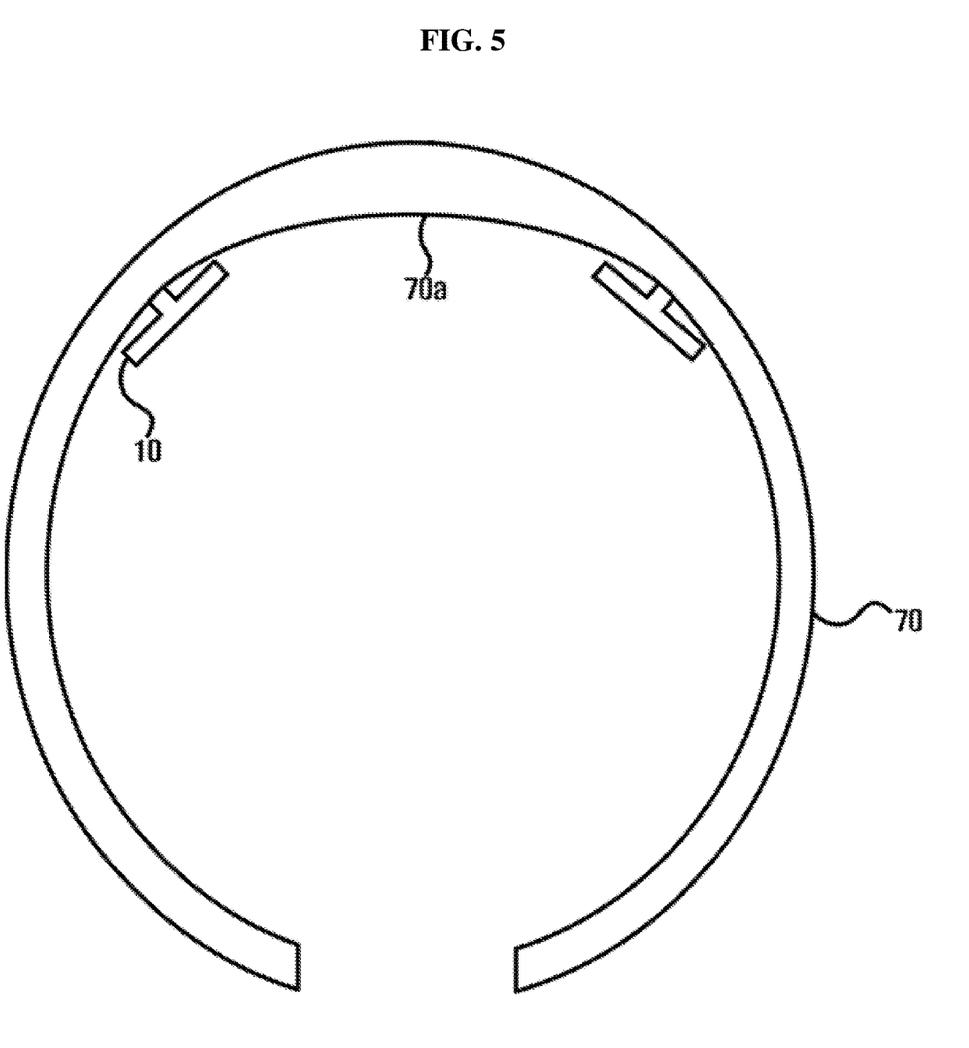
FIG. 5 is a diagram illustrating the electric device according to the third exemplary embodiment of the present invention.

In reference with FIG. 5, the electric device according to a third exemplary embodiment of the present invention will be explained in the following. The explanation will be mainly focused only on the difference from FIG. 1. FIG. 5 is a diagram illustrating the electric device according to the third exemplary embodiment of the present invention.

FIG. 5 is showing the exemplary embodiment of the appearance of the electric device. The components illustrated by FIG. 1 to FIG. 4 may be applicable to the electric device of FIG. 5.

In reference with FIG. 5, the electric device may include a frame 70, and an electrode module 10 attached to the frame 70. In particular, since the electrode module 10 can be attached to the inside 70a of the frame 70, the microelectrode 11 of the electrode module 10 can be attached to a user's head when the user wears the electric device on, or has it attached to his/her head. Although the present description is exemplifying the electric device stimulating the head, the technical features of the present invention may also apply to the electric device stimulating the user's body parts other than the head. In addition, the overall appearance of the electric device is not limited to that of FIG. 5.

In reference with FIG. 6, the electric device according to a forth exemplary embodiment of the present invention will be explained in the following. The explanation will focus only on the difference from FIG. 5. FIGS. 6A and 6B are diagrams illustrating the electric device according to the forth exemplary embodiment of the present invention.

Figure 6A:
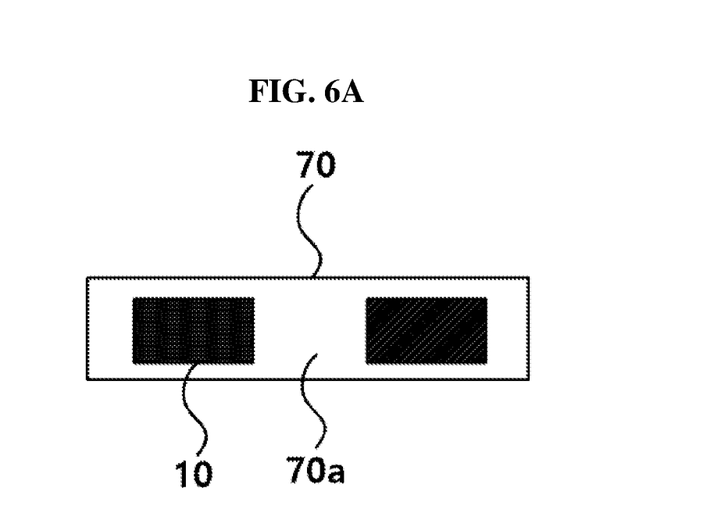
FIGS. 6A and 6B are diagrams illustrating the electric device according to the forth exemplary embodiment of the present invention.
Figure 6B:
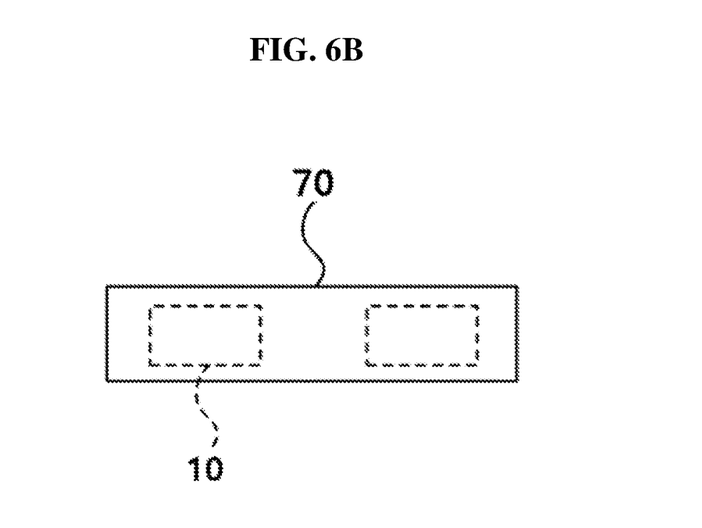

FIGS. 6A and 6B are illustrating an exemplary embodiment of the appearance of the electric device. The components shown by FIG. 1 to FIG. 4 can be also applied to the electric device of FIGS. 6A and 6B.

In reference with FIGS. 6A and 6B, the electric device of the present exemplary embodiment may include a frame 70 and an electrode module 10 adhered to a user's skin when the user has the electric device attached thereon. However, the frame 70 of the electric device of the present exemplary embodiment may be a band-typed, differently from that of the electric device shown by FIG. 5.

In particular, since the electrode module 10 can be attached to the inside 70a of the frame 70, the microelectrode 11 of the electrode module 10 can be adhered to a subject's head when the subject has the electric device attached on the head. In the present description, the electric device stimulating the user's head is exemplified; however, the technical features of the present invention are also applicable to the electric device stimulating the body parts other than the head.

According to the present invention described above, when measuring an EEG signal or applying electric stimulation to a subject's head, the electric device can adjust in detail a measuring or stimulating position by using a plurality of microelectrodes forming an electric array.

In addition, as an EEG measuring device and an electric stimulation device are combined, it is possible to measure an EEG signal from a subject's head and to apply electric stimulation thereto.

Also, it is possible to estimate an EEG signal from the area not directly attached to a plurality of electrodes and thus difficult to measure.

It is to be understood that the invention is not limited to the disclosed embodiments, but on the contrary, is intended to cover various modification and the equivalent arrangements which can be implemented by the ordinary skilled in the art within the spirit and the scope of the appended claims.

In case part of the sense parts is out of order, the malfunctioning sense part can be replaced and there is no need to replace the device for rehabilitation exercise of the hands, which would reduce maintenance cost of the device.

The term "module" used in this disclosure may refer to a certain unit that includes one of hardware, software and firmware or any combination thereof. The module may be interchangeably used with unit, logic, logical block, component, or circuit, for example. The module may be the minimum unit, or part thereof, which performs one or more particular functions. The module may be formed mechanically or electronically.

As described above, part of the method (e.g., operations) or system (e.g., modules or functions) according to various embodiments can be implemented with command instructions that can be conducted via various types of computers and stored in computer-readable storage media, as types of programming modules, for example. One or more processors (e.g., control module 20) can execute commend instructions, thereby performing the functions. An example of the computer-readable storage media may be memory (or database).

Examples of computer-readable media include: magnetic media, such as hard disks, floppy disks, and magnetic tape; optical media such as CD-ROM disks and DVDs; magneto-optical media; and hardware devices that are specially configured to store and perform program instructions (programming modules), such as read-only memory (ROM), random access memory (RAM), flash memory, etc. Examples of program instructions include machine code, such as produced by a compiler, and files containing higher level code that may be executed by the computer using an interpreter. The described hardware devices may be configured to act as one or more software modules in order to perform the operations and methods described above, or vice versa.

Modules or programming modules according to various embodiments may include one or more components, remove part of them described above, or include new components. The operations performed by modules, programming modules, or the other components, according to the present disclosure, may be executed in serial, parallel, repetitive or heuristic fashion. Part of the operations can be executed in any other order, skipped, or executed with additional operations.

Although example embodiments of the disclosure have been described in detail above, it should be understood that many variations and modifications of the basic inventive concept herein described, which may be apparent to those skilled in the art, will still fall within the example embodiments of the disclosure as defined in the appended claims. The above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware. The computer, the processor, microprocessor controller or the programmable hardware include memory components, e.g., RAM, ROM, Flash, etc. that may store or receive software or computer code that when accessed and executed by the computer, processor or hardware implement the processing methods described herein.

While exemplary embodiments have been particularly shown and described, it will be understood by those of ordinary skill in the art that various changes in form and details may be made therein without departing from the spirit and scope of the present inventive concept as defined by the following claims.

What is claimed is:

1. An electric device for measuring an Electroencephalogram (EEG) signal from a subject's head, the electric device comprising:

a plurality of electrode units configured to be attached to each different position of the head of the subject and configured to detect the EEG signal from the subject's head, and wherein each of the plurality of electrode units includes a plurality of microelectrodes forming an electric array;

an electric stimulation unit configured to supply electric current in order to provide the electric stimulation to the subject's head;

a switching unit connected to the plurality of electrode units, and configured to switch the each of the plurality of electrode units to be selectively connected and each of the plurality of microelectrodes to be selectively connected;

a controller connected to the switching unit, and configured to control the switching unit to be selectively connected to the each of the plurality of the electrode units to receive the EEG signal from the subject's head through connected electrode unit among the plurality of electrode units, wherein the controller is configured to receive a first plurality of EEG signals detected from a first plurality of microelectrodes included in a first electrode unit among the plurality of electrode units, receive the first plurality of EEG signals detected from first area of the subject's head, through the switching unit, select at least one microelectrode, which is configured to simultaneously receive the EEG signal from the subject's head and supply the electric current to the subject's head, from the first plurality of microelectrodes, based on the received first plurality of EEG signals, receive a first EEG signal from the subject's head through the selected at least one microelectrode among the first plurality of microelectrodes, and control, at the same time as receiving the first EEG signal, the switching unit to supply the electric current to the subject's head through the selected at least one microelectrode.

2. The electric device of claim 1, wherein the plurality of electrode units is configured to supply the electric current to the each different position, and wherein the controller is configured to control the switching unit to selectively supply, through the switching unit and the connected electrode unit, the electric current from the electric stimulation unit to the subject's head.

3. The electric device of claim 2, wherein the controller is configured to control the switching unit to supply the electric current from the electric stimulation unit to the subject's head through the each of the plurality of the microelectrodes.

4. The electric device of claim 3, wherein the controller is configured to select the at least one microelectrode from the first plurality of microelectrodes by comparing signal strength of the first plurality of EEG signals detected from the first plurality of microelectrodes with a standard EEG signal.

5. The electric device of claim 3, further comprising a data storage connected to the controller, and configured to store EEG data previously detected from the subject's head,
   wherein the EEG data includes information on detected position in the subject's head where the EEG data have been obtained, and
   wherein the controller is configured to determine, based on the stored EEG data and the first plurality of EEG signals detected from the first plurality of microelectrodes included in the first electrode unit attached to a first area of the subject's head, a position of the first area in the subject's head.

6. The electric device of claim 1, further comprising a patch formed on the plurality of the microelectrodes.

7. The electric device of claim 1, wherein the electric device is adapted to be worn on the subject's head.

* * * * *